United States Patent [19]

König et al.

[11] 4,118,483

[45] Oct. 3, 1978

[54] PEPTIDES HAVING GONADOLIBERIN ACTIVITY AND PROCESS FOR THEIR MANUFACTURE

[75] Inventors: Wolfgang König, Hofheim; Rolf Geiger, Frankfurt am Main; Jürgen Sandow, Königstein, all of Fed. Rep. of Germany

[73] Assignee: Hoechst Aktiengesellschaft, Frankfurt am Main, Fed. Rep. of Germany

[21] Appl. No.: 789,253

[22] Filed: Apr. 20, 1977

[30] Foreign Application Priority Data

Apr. 22, 1976 [DE] Fed. Rep. of Germany ....... 2617646

[51] Int. Cl.$^2$ ..................... A61K 37/00; C07C 103/52
[52] U.S. Cl. ........................... 424/177; 260/112.5 LH
[58] Field of Search ............... 260/112.5 LH; 424/177

[56] References Cited

U.S. PATENT DOCUMENTS

| 4,003,884 | 1/1977 | Konig et al. | 260/112.5 LH |
| 4,024,248 | 5/1977 | Konig et al. | 260/112.5 LH |

FOREIGN PATENT DOCUMENTS 2,438,350  2/1976  Fed. Rep. of Germany ........ 260/112.5 LH Primary Examiner—Delbert R. Phillips
Attorney, Agent, or Firm—Curtis, Morris & Safford

[57] ABSTRACT

A peptide with LH-RH-activity which is a LH-RH-peptide wherein Gly in 6-position is replaced by D-glutaminic-acid which may be N-substituted at the CO-NH$_2$ moiety, wherein in 10-position Gly-NH$_2$ may be replaced by a NH-alkyl or NH-cycloalkyl group and/or wherein the amino acids in 4-, 5-, 7- and/or 8-position may be replaced by other amino acids and a process for its manufacture.

6 Claims, No Drawings

PEPTIDES HAVING GONADOLIBERIN ACTIVITY AND PROCESS FOR THEIR MANUFACTURE

The releasing hormone, gonadoliberin, of the structure

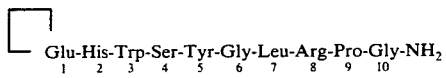

(Biochem. Biophys. Res. Commun. 43, 1334 (1971)) which releases the luteinizing hormone (LH) and the follicle stimulating hormone (FSH), has already been modified in many positions. Thus, it has been found, inter alia, that by replacing Gly in position 6 by lipophilic D-amino acids having branched side chains such, for example, as D-leucine or D-Ser(Bu$^t$), the biological activity can be strongly increased (Peptides, Proceedings of the 4th American Peptide Symposium 1975, pages 883-888, Ed.: R. Walter and J. Meienhofer). Substitutions having hydrophilic side chains such, for example, as D-Ser or D-Glu having been found less favorable.

It has now been found that, surprisingly gonadoliberin analogues having the hydrophilic D-glutamine or derivatives thereof in position 6 surpass the biological action of the above mentioned highly active compounds.

The subject of the invention is peptides of the general formula I

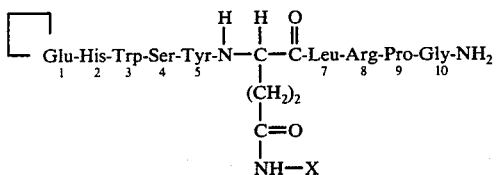

in which the amino acid in position 6 has the D-configuration, X represents hydrogen or a branched or straight chain alkyl or cycloalkyl radical containing 1-10 carbon atoms, which is optionally substituted by optionally substituted phenyl, hydroxyl or carboxyl groups, which may also be present as esters or amides, and/or the Gly-NH$_2$ group in the 10-position is replaced by an NH-alkyl radical containing 1-3 carbon atoms or the NH-cyclopropyl residue, which may be substituted by OH or fluorine atoms, and wherein optionally Ser may be replaced by Ala or Thr, Tyr by Phe, Leu by Cys(Bu$^t$), Ser(Bu$^t$), Glu(OBu$^t$) or Asp(OBu$^t$), Arg by Lys, Orn or homoarginine.

The subject of the invention is also a process for the production of compounds of the general formula I, which is ccharacterised in that (a) the appropriate peptide fragments are condensed in accordance with the condensation scheme 1-3 + 4-10 or 1-2 + 3-10 by methods customary in peptide chemistry, or (b) a peptide of the formula Ii

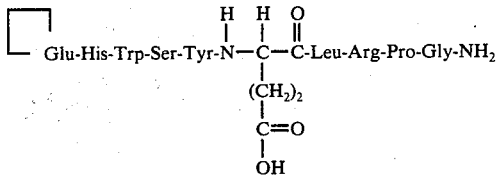

in which individual amino acids corresponding to formula I may be exchanged, is reacted with primary amines of the formula NH$_2$X in the presence of condensing agents customary in peptide chemistry.

As amine components —NHX of the D-glutamic acid alkylamides in position 6 there come into consideration primary amines of which the alkyl radical may be substituted by optionally substituted phenyl radicals or hydroxyl groups such, for example, as methylamine, ethylamine, n-propylamine, isopropylamine, n-butylamine, iso-butylamine, tert.-butylamine, n-hexylamine, n-octylamine, adamantylamine, cyclopropylamine, 2-amino-hexahydro toluene, 4-amino-hexahydro toluene, ethanolamine, 1-aminopropanol-2, 2-amino-2-methylpropanol, benzylamine, benzhydrylamine, 4-methoxybenzylamine, 2,4-dimethoxy-benzylamine, 4,4'-dimethoxybenzhydrylamine, 4,4'-dimethylbenzhydrylamine or β-phenylethylamine.

Of special importance are compounds of the formula I, in which X represents a cycloalkyl radical containing 5 to 8 carbon atoms, especially the cyclohexyl radical.

As amine components —NHX, in which X represents a carboxyl-substituted alkyl radical, there come into consideration α- and β-amino acids, especially naturally occurring α-amino acids. The carboxyl groups of these amino acids may be present in the form of amides or esters, and there come into consideration as esters those of primary or secondary alcohols or, for example, also of hydroxy-steriods such as estradiol, testosterone and others.

Analogues having an especially long activity are compounds in which additionally Gly—NH$_2$ in the 10-position is replaced by HN—C$_2$—H$_5$ or NH-cyclopropyl.

The LH-RH analogues of the invention are superior to the also strongly active D-Ser(Bu$^t$)$^6$-analogues, owing to their greater stability to acid, which can be an advantage in oral administration.

In the coupling of fragments under (a), there is preferably used the azide coupling that takes place without racemization or the DCC-method with the use of racemization-lowering additives such, for example, as 1-hydroxybenzotriazole, 3-hydroxy-4-oxo-3,4-dihydro-1,2,3-benzotriazine, N-hydroxysuccinimide or N-hydroxy-5-norbornen-endo-2,3-dicarboximide.

In uniting [D-Glu$^6$] gonadoliberin analogues with primary amines under (b), practically all peptide uniting reagents, which unite under mild reaction conditions, can be used. There come into consideration, for example, N,N'-carbonyldiimidazole, DCC (especially advantageously with the addition of 1-hydroxybenzotriazole), N-ethoxycarbonyl-2-ethoxy-1,2-dihydroquinoline or Woodward's reagent K (N-ethyl-5-phenylisoxazolium 3'-sulphonate).

As intermediate amino-protecting groups there may be mentioned groups which can be dehydrogenated such, for example, as the benzyloxycarbonyl radical (= Z-radical) or groups which can be cleaved under weakly acid conditions such, for example, as the 2-(para-diphenyl)-isopropyloxycarbonyl radical or 2-(3,5-dimethoxyphenyl)-isopropyloxycarbonyl radical. For the acid-stable glutaminic acid amides, there may be mentioned as an intermediate amino-protectinng group also the tert.-butyloxycarbonyl radical.

In the last peptide coupling to form the compounds of the invention the third functions of the trifunctional amino acids are advantageously unprotected (for example, Arg, Tyr, Ser, His). However, during the synthesis of the fragments the third functions may be suitably protected. The guanidofunction of arginine may be blocked, for example, by a nitro group, which is split off in the next following hydrogenation. However, it may also be blocked by groups capable of being split off under acid conditions such as the carbobenzoxy radical or the tosyl radical.

The hydroxyl group of tyrosine is intermediately protected advantageously by the benzyl radical, which can be dehydrogenated, or by the tert.-butyl radical, which can be acid-cleaved.

The compounds of the invention are medicaments, which in hypothalamus- and hypopghysis-insufficiency cause the secretion of the luteinizing and the follicle stumulating hormone from the anterior lobe of the hypophysis, and are therefore used for the treatment of female and male sterility, provided that this is of hypophysary origin. A further use of the substances of the invention is fixing the time of ovulation in a woman. Shortly befoe the expected time of ovulation it is possible by the administration of the new medicaments to bring about ovulation with certainty. This is of importance for family planning both by the method of Knaus-Ugino and also for artificial insemination. The compounds are also especially important for veterinary medicine in connection with insemination and estral synchronisation.

The compounds of the invention, when dissolved in physiological sodium chloride solution, can be administered intravenously, intramuscularly and subcutaneously, they can be used for intranasal administration in the form of nasal drops or nasal spray and also for rectal or vaginal administration. At high doses they also act orally and buccally.

The preferred dosages used for various types of administration are:
intravenous: 20 – 500 ng/kg
subcutsaneoud: 20 – 500 ng/kg
intramuscular: 20 – 500 ng/kg
intransal: 1000 – 50000 ng/kg
rectal: 2000 – 100000 ng/kg
vaginal: 2000 – 100000 ng/kg
oral/buccal: 1000000 ng/kg

EXPERIMENTAL PART

The chromatographic purity was tested over thin layer plates (silica gel F-254) of the firm Merck.
Eluting agent 1: Chloroform/methanol/glacial acetic acid/ water as 60:45:61:14.
Eluting agent 2: Butanone/pyridine/water/glacial acetic acid as 70:15:15:2.

ABBREVIATIONS

Most of the abbreviations correspond to the proposals of the IUPACIUB Commission on Biochemical Nomenclature (Hoppe Seyler's Z. Physiol. Chem. 348, 258 (1976); J. Biol. Chem. 247, 977 (1972)).
Further abbreviations:

DDC = Dicyclohexylcarbodiimide.
DCHA = Dicyclohexylamine.
Mbh = 4,4'-Dimethoxybenzhydryl group.
OObt = 3-Hydroxy-4-oxo-3,4-dihydro-1,2,3-benzotriazone ester.
OTcp = 2,4,5-Trichlorophenyl ester.

The following Examples illustrate the invention.

EXAMPLE 1

Glu-His-Trp-Ser-Tyr-D-Gln(Mbh)-Leu-Arg-Pro-NH—$C_2H_5$.

(a) Z-D-Gln(Mbh)-OBzl

To a solution of 18.55 grams (52.4 mmol) of Z-D-Glu-OBzl, 14 grams (50 mmol) of 4,4'-dimethoxybenzhydrylamine hydrochloride, and 6.76 grams (50 mmol) of 1-hydroxybenzotriazole in 100 ml of dimethylformamide are added at 0° C. 6.5 ml of N-ethylmorpholine (50 mmol) and 11 grams of DCC. The mixture is stirred for 2 hours at 0° C. and allowed to stand overnight at room temperature. The precipitate formed is filtered off with suction, and the filtrate is concentrated. The residue is triturated with a saturated solution of $NaHCO_3$, filtered off with suction, washed with water and dried. For purification the product is boiled with isopropanol, cooled, filtered with suction and washed with isopropanol and petroleum ether.

Yield: 17.3 grams (58%), melting point 208°, $[\alpha]^{20}_D = -2.7°$ (c = 1, in glacial acetic acid)
$C_{35}H_{36}N_2O_7$ (596.7) Calculated: C 70.45: H 6.08: N 4.70. Found: C 70.7: H 6.2: N 4.8.

(b) Z-D-Gln(Mbh)-OH 54.2 Grams (91 mmol) of Z-D-Gln(Mbh)-OBzl are suspended in 640 ml of dioxane and 130 ml of water. This suspension is titrated with 95.6 ml of 1n-MaOH (thymolphthalein as indicator). The suspension is then neutralised and concentrated. The residue is acidified with 2n-hydrochloric acid to a PH-value of 2-3, and triturated with water, filtered off with suction, and the residue is washed well with water and dried. The substance is dissolved in ethyl acetate while warming Insoluble matter is filtered off with suction. The filtrate is concentrated until crystallisation begins. The precipitation is completed with petroleum ether. It is then recrystallised once from ethyl acetate/petroleum ether.
Yield: 37.8 grams, melting at 118°–129°, $[\alpha]^{22}_D = +6.75°$ (c = 2, in dimethylformamide).

(c) Z-D-Gln(Mbh)-OTcp

To a solution of 5.06 grams (10 mmol) of Z-D-Gln(Mbh)-OH and 2.17 grams (11 mmol) of 2,4,5-trichlorophenol in 20 ml of dimethylformamide are added at 0° C. 2.2 grams of DCC, the mixture is allowed to stand for 2 hours at 0° C. and 2 hours at room temperature. The precipitate is filtered off with suction, and the filtrate is concentrated. The residue is triturated with isopropanol, filtered off with suction ans washed with petroleum ether. Yield 5.2 grams, melting point 181°.
$C_{34}H_{31}N_2O_7Cl_3$ (686.0), Calculated: C 59.53: H 4.56: N 4.08. Found: C 59.8: H 4.6: N 4.1.

(d) H-D-Gln(Mbh)-Leul-Arg-Pro-NH-$C_2H_5$·2HCl

To a solution of 5.4 grams (7.15 mmol) of H-Leu-Arg-Pro-NH-$C_2H_5$-ditosylate, 965 mg of 1-hydroxybenzotriazole and 1.86 ml of N-ethyl-morpholine in 50 ml of dimethylformamide are added 4.9 grams of Z-D-Gln(Mbh)-OTcp. The mixture is allowed to stand overnight at room temperature, the solution is concentrated and the residue is triturated with saturated NaHCO₃ solution and water. The still not quite dry substance is dissolved in methanol with the addition of some dimethylformamide. A spatula tip of Pd/BaSO₄ catalyst is added and hydrogenation is carid out by passing hydrogen through the solution while stirring. The pH-value of the solution is maintaind at 4.5 by means of an autotitrator by the addition of 1n-methanolic hydrochloric acid. When the hydrogenation is complete, the catalyst is filtered off with suction and the filtrate is concentrated. The residue is triturated with ether and filtered off with suction. Yield: 5.3 grams of amorphous substance.

(e) H-Tyr-Ser-D-Gln(Mbh)-Leu-Arg-Pro-NH-C₂H₅.2HCl

To a solution of 2.7 grams (3.2 mmol) of H-D-Gln(Mbh)-Leu-Arg-Pro-NH-C₂H₅.2 HCl, 1.58 grams (3.2 mmol) of Z-Ser-Tyr(Bzl)-OH and 432 mg (3.2 mmol) of 1-hydroxybenzotriazole in as little dimethylformamide as possible are added at 0° C. 0.83 ml (6.4 mmol) of N-ethylmorpholine and 704 mg of DCC, the mixture is stirred for one hour at 0° C. and allowed to stand overnight at room temperature, the precipitate is filtered off with suction and the filtrate is concentrated in vacuo. The residue is triturated twice with a saturated NaHCO₃ solution, distilled with absolute alcohol and triturated with ether. Yield: 3.9 grams of amorphous material, which is catalytically hydrogenated in a manner analogous to recipe 1d. The residue is urified by partition chromatography over Sephadex LH 20 (glacial acetic acid/n-butanol/water as 4:8:40). Yield: 1.47 grams of amorphous freezedried substance, $[\alpha]_D^{20} = -33.7°$ (c = 1, in methanol).

(f)

Glu-His-Trp-Ser-Tyr-D-Gln(Mbh)-Leu-Arg-Pro-NH—C₂H₅-diacetate.

To a solution of 250 mg of

Glu-His-Trp-NH—NH₂ in 3 ml of dimethylformamide are added at −30° C. 0.33ml of a 6.05n-HCl/dioxane solution and 0.6 ml of a solution of 10 percent. strength of tert.-butyl nitrite in absolute dioxane.

The mixture is stirred for 20 minutes at −10° C. and at −40° C. 544.6 mg of H-Ser-Yyr-D-Gln(MbH)-Leu-Arg-Pro-NH-C₂H₅.2HCl and 0.39 ml of N-ethylmorpholine are added. The mixture is allowed to stand overnight in a cooling chamber at 4° C., then concentrated and the residue is triturated with ether. The crude product is converted over a small Dowex 1×2-column (acetate form) into the acetate, and purified twice in a manner analogous to Example 1e by partition chromatography over Sephadex LH 20. Yield: 120 mg.

Amino acid analysis (hydrolysis for 68 hours in 6n-HCl at 110° C):

Glu (1.86), His (0.96), Ser (0.85), Tyr (0.82), Leu (0.96),
Arg (1.00), Pro (0.95).

EXAMPLE 2

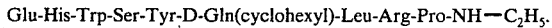
Glu-His-Trp-Ser-Tyr-D-Gln(cyclohexyl)-Leu-Arg-Pro-NH—C₂H₅.

(a) Z-D-Gln(cyclohexyl)-OBzl

To a solution of 12.3 grams (33.1 mmol) of Z-D-Glu-OBzl, 4.06 ml (33.1 mmol ) of cyclohexlamine and 4.47 grams of 1-hydroxybenzotriazole (33.1 mmol) in 50 ml of absolute tetrahydrofurane are added at 0° C. 7.35 grams of DCC, the mixture is allowed to stand for 2 hours at 0° C. and overnight at room temperature. On the next day, the precipitate is filtered off with suction, washed with tetrahydrofurane and the filtrate is concentrated. The residue is triturated with a saturated NaHCO₃ solution, filtered off with suction and washed well with water and dried. Yield: 14.5 grams, melting point 150°. After recrystallisation from isopropanol/petroleum ether: 6 grams, melting point 163°, $[\alpha]_D^{20} = +1°$ (c = 1, in glacial acetic acid).

(b) Z-D-Gln(Cyclohexyl)-OH

6 Grams of Z-D-Gln(cyclohexyl-OBzl are suspended in 100 ml of dioxane/water (4:1) and triturated with 1n-NaOH (thymolphthalein as indicator, consumption: 14 ml of 1n-NaOH). Neutralisation with 1n-HCl is then carried out and concentration in vacuo. The residue is distributed between ethyl acetate and 1n-HCl. The ethyl acetate phase is washed with water, dried and concentrated. The residue is triturated with ether and filtered off with suction. Yield: 4.3 grams. melting at 112-115°, $[\alpha]_D^{20} = +6.2°$ (c = 1, in methanol).

(c) H-Ser-Tyr-D-Gln(cyclohexy)-Leu-Arg-Pro-NH-C₂H₅.2HCl

To a solution of 1.89 grams (5 mmol) of Z-D-Gln(cyclohexyl)-OH, 3,6 grams (5 mmol) of H-Leu-Arg-Pro-NH-C₂H₅-ditosylate and 1.35 grams (10 mmol) of 1-hydroxybenzotriazole in 20 ml of dimethylformamide are added at 0° C. 1.3 ml of N-ethylmorpholine and 1.1 grams of DCC. The mixture is stirred for one hour at 0° C. and allowed to stand overnight at room temperature. The reaction product precipitates out together with the dicyclohexyl-urea. Ether is added to the reaction mixture and the precipitate is filtered off with suction. The filter cake is triturated with saturated NaHCO₃ solution and filtered off with suction. Yield: 3.2 grams of an amorphous material, which is catalytically hydrogenated in methanol with a Pd-catalyst in a manner analogous to that in Example 1d. When the hydrogenation is complete the catalyst is filtered off with suction, the filtrate is concentrated and the residue is triturated with ether. Yield: 2.2 grams of an amorphous material, which without further purification is dissolved in a small amount of dimethylformamide with 1.5 grams of Z-Ser-Tyr(Bzl)OH and 405 mg of 1-hydroxybenzotriazole. To this solution are added 0.78 ml of N-ethylmorpholine and at 0° C. 660 mg of DCC. The mixture is stirred for one hour at 0° C. and overnight at room temperature. The precipitate is filtered off with suction and the filtrate is concentrated. The residue is triturated with saturated NaHCO₃ solution, filtered off with suction and washed with water. Yield: 2.6 grams of an amorphous material, which without purification is catalytically hydrogenated in a mixture of dimethylformamide and methanol (1:1) in a manner analogous to that in Example 1d. When the hydrogenation is complete, the catalyst is filtered off with suction and the filtrate is concentrated. The residue is triturated with ehter and then purified by partition chromatography. Yield: 420 mg of a tin layer chromatographically unitary, ninhydrin-positive compound having the correct amino acid analysis. (Eluting agent 1).

⌐¬
└ Glu-His-Trp-Ser-Tyr-D-Gln(cyclohexyl)-Leu-Arg-Pro-NH—C$_2$H$_5$-diacetate.

215 mg of

⌐¬
└ Glu-His-Trp-NH—NH$_2$ are reacted in a manner analogous to that in Example 1f with 420 mg of H-Ser-Tyr-D-Gln(cyclohexyl)-Leu-Arg-Pro-NH-C$_2$H$_5$.2HCl and converted into the acetate. The compound is purified by gradient elution over a column (100 × 1.5 cm) of carboxymethyl-cellulose with an 0.002-0.01n-ammonium acetate buffer as eluting agent. There were isolated 128.3 mg of thin layer chromatographically pure product (Eluting agent 1). Content of peptide base according to UV-spectrum and amino acid analysis: 80%. The remainder is water (10%) and acetic acid (10%). $[\alpha]_D^{20} = -33.4°$ (c = 1, in water).

Amino acid analysis (hydrolysis for 68 hours in 6n-HCl at 110° C.):

Ser (0.7), Glu (2.0), Pro (0.9), Leu (1.0), Tyr (0.9), His (1.0), Arg (1.0). The Trp-content is determined by UV-extinction (1.0).

⌐¬
└ Glu-His-Trp-Ser-Tyr-D-Gln(Bzl)-Leu-Arg-Pro-NH—C$_2$H$_5$.

(a) Z-D-Gln(Bzl)-OBzl

To a solution of 11.4 grams of Z-D-Gln-OBzl and 4.15 grams of 1-hydroxybenzotriazole in 50 ml of absolute tetrahydrofurane are added 3.35 ml of benzylamine and 6.76 grams of DCC. The mixture is stirred for 1 hour at 0° C and 1 hour at room temperature, the precipitate is filtered off with suction and the filtrate is concentrated. The residue is triturated in succession with NaHCO$_3$ solution, 2n-HCl NaHCO$_3$ solution and water, filtered off with suction and washed with water.

Yield: 16.2 grams, melting point 144°. For purification recrystallisation from isopropanol is carried out. The product is washed with petroleum ether. Yield: 6 grams, melting point 149°, $[\alpha]_D^{20} = -0.1$ (c = 1, in glacial acetic acid.

(b) Z-D-Gln(Bzl)-OH

6 Grams of Z-D-Gln(Bzl)-OBzl are suspended in 100 ml of dioxane/water (4:1) and titrated with 1n-sodium hydroxide solution (thymolphthalein as indicator). Consumption: 13 ml of 1n-NaOH. Neutralisation with 2n-HCl and concentration are then carried out. The residue is distributed between ethyl acetate and 2n-HCl. Insoluble matter is filtered off with suction. The ethyl acetate phase is washed with water, dried with sodium sulphate and concentrated. The residue is triturated with ether and filtered off with suction. Yield: 3.05 grams melting at 80°–110°.

(c) H-D-Gln(Bzl)-Leu-Arg-Pro-NH-C$_2$H$_5$.2 HCl

To a solution of 3.6 grams of H-Leu-Arg-Pro-NH-C$_2$H$_5$-ditosylate, 1.93 grams of Z-D-Gln(Bzl)-OH and 1.35 grams of 1-hydroxybenzotriazole in 20 ml of dimethylformamide are added 1.3 ml of N-ethylmorpholine and at 0° C. 1.1 grams of DCC, and the mixture is stirred for 1 hour at 0° C. and overnight at room temperature. The precipitate is filtered off with suction, the filtrate is concentrated and the residue is triturated twice with a solution of sodium bicarbonate and dissolved in methylene chloride. The solution is dried with sodium sulphate and concentrated. The residue is triturated with ether. Yield: 3.3 grams of an amorphous material, which without furthher purification is catalytically hydrogenated in methanol with a Pd catalyst in a manner analogous to that in Example 1d. The catalyst is filtered off with suction and the filtrate is concentrated, and trituration with ether is carried out. The very impure material is purified by partition chromatography in a manner analogous to that in Example 1e. Yield: 910 mg of ninhydrinpositive, thin layer chromatographically unitary substance (eluting agent 2) having the correct amino acid analysis.

(d) H-Ser-Tyr-D-Gln(Bzl)-Leu-Arg-Pro-NH-C$_2$H$_5$

To a solution of 718.7 mg of H-D-Gln(Bzl)-Leu-Arg-Pro-NH-C$_2$H$_5$.2 HCl in 2 ml of dimethylformamide are added at room temperature 0.26 ml of N-ethylmorpholine and 637.6 mg of Z-Ser-Tyr(Bzl)-OObt. The mixture is allowed to stand overnight at room temperature, concentrated and the residue is triturated twice withh a saturated solution of sodium bicarbonate. It is reprecipitated from methanol/ether and filtered off with suction. Yield: 1 gram of an amorphous substance, which without further purification is catalytically hydrogenated in a methanol-dimethylformamide-mixture (1:1) with a Pd-catalyst in a manner analogous to that in Example 1d. The catalyst is filtered off wth suction and the filtrate is concentrated. The residue is triturated with ether. Yield: 810 mg of a ninhydrin-positive compound (eluting agent 2) having only traces of impurities and having the correct amino acid analysis.

(e)
⌐¬
└ Glu-His-Trp-Ser-Tyr-D-Gln(Bzl)-Leu-Arg-Pro-NH—C$_2$H$_5$-diacetate.

250 mg of

⌐¬
└ Glu-His-Trp-NH—NH$_2$ are reacted in a manner analogous to that in Example 1f with 484.5 mg of H-Ser-Tyr-D-Gln(Bzl)-Leu-Arg-Pro- NH-C₂H₅.2 HCl and converted into the acetate. The crude compound is purified by gradient elution over a column (100 × 1.5 cm) of carboxymethylcellulose with an 0.002–0.01 n-ammonium acetate buffer as eluting agent and by partition chromatography in a manner analogous to that in Example 1e. Yield: 181.3 mg of thin layer chromatographically pure product (eluting agent 1). According to the UV-spectrum: 82% of peptide base. The remainder is water (10%) and acetic acid (8%). $[\alpha]_D^{20} = -48.4°$ (c = 1, in water).

Amino acid analysis (hydrolysis for 68 hours in 6n-HCl at 110° C.):

Ser (0.7), Glu (2.0), Pro (0.9), Leu (1.0), Tyr (0.9), His (1.0), Arg (1.0). The Trp-content (1.0) was determined by UV-extinction.

EXAMPLE 4

 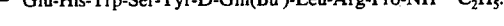
Glu-His-Trp-Ser-Tyr-D-Gln(Buᵗ)-Leu-Arg-Pro-NH—C₂H₅.

(a) Z-D-Gln(Buᵗ)-OBzl

To a solution of 9.9 grams of Z-D-Glu-OBzl and 3.6 grams of 1-hydroxybenzotriazole in 50 ml of absolute tetrahydrofurane are added 1.96 grams of tert.-butylamine and at 0° C. 5.86 grams of DCC. The mixture is stirred for 2 hours at 0° C. and overnight at room temperature. The next day the precipitate is filtered off with suction and the filtrate is concentrated. The residue is dissolved in ethyl acetate and the solution is washed in succession with a saturated solution of sodium bicarbonate, 2n-HCl, a saturated solution of sodium bicarbonate and water, dried with sodium sulphate and concentrated. Yield: 4.6 gams of an oil.

(b) Z-D-Gln(Buᵗ)-OH·DCHA 4.6 Grams of Z-D-Gln(Buᵗ)-OBzl are dissolved in 75 ml of a dioxane/water mixture (4:1) and tritrated with 1n-NaOH (indicator: thymolphthalein). Consumption off 1n-NaOH: 10.8 ml. The solution is then neutralized with 2n-HCl and the reaction mixture is concentrated in vacuo. The residue is distributed between ethyl acetate and 2n-HCl. The ethyl acetate phase is washed with water, dried with sodium sulphate and concentrated. The rsidue is dissolved in ether and the salt is precipitated with dicyclohexylamine. Yield: 4.2 grams. Melting point 143°, $[\alpha]_D^{20} = -10.2°$ (c = 1, in methanol).

(c) H-D-Gln(Buᵗ)-Leu-Arg-Pro-NH-C₂H₅.2 HCl 5.3 Grams of Z-D-Gln(Buᵗ)-OH·DCHA are distributed between ether and KHSO₄ solution. The ether phase is washed with water, dried over sodium sulphate and concentrated. The oil that remains behind is dissolved together with 7.2 grams of H-Leu-Arg-Pro-NH-C₂H₅-ditosylate, 1.35 grams of 1-hydroxybenzotriazole and 2.6 ml of N-ethylmorpholine in 20 ml of dimethylformamide. At 0° C. 2.2 grams of DCC are added, and the mixture is stirred for one hour at 0° C. and allowed to stand overnight at room temperature. The precipitate is filtered off with suction and the filtrate is concentrated. The residue is triturated twice withh sodium bicarbonate solution and then dissolved in methylene chloride. The solution in dried wiith sodium sulphate and concentrated. The residue is triturated with petroleum ether and filtered off with suction. Yield: 6.8 grams of an amoprhous substance, which without further purification is catalytically hydrogenated in methanol in a manner analogous to that in Example 1d. When the hydrogenation is complete, the catalyst is filtered off with suction and the filtrate is concentrated. The residue is triturated with ether and filtered off with suction. Yield: 6.82 grams. The substance was very impure and was purified by partition chromatography in a manner analogous to that in Example 1e. Yield: 3.15 grams of an amorphous thin layer chromatographically unitary substance (eluting agent 2) having the correct amino acid analysis.

(d) H-Ser-Tyr-D-Gln(Buᵗ)-Leu-Arg-Pro-NH-C₂H₅.2 HCl 3.13 Grams of H-D-Gln(Buᵗ)-Leu-Arg-Pro-NH-C₂H₅ are dissolved in 10 ml of dimethylformamide. 1.2 ml of N-ethylmorpholine and 2.98 grams of Z-Ser-Tyr(Bzl)-OObt are added. The mixture is allowed to stand overnight at room temperature, filtered to remove insoluble matter, the filtrate is concentrated and the residue is triturated twice with a saturated solution of sodium bicarbonate and once with water. Yield: 6 grams of an amorphous substance, which without further purification is catalytically hydrogenated in a dimethylformamide/methanol mixture(1:1) with a Pd-catalyst in a manner analogous to that in Example 1d. When the hydrogenation is complete, the catalyst is filtered off with suction and the filtrate is concentrated. The residue is triturated with ether and then purified by partition chromatography in a manner analogous to that in Example 1e. Yield: 1.6 grams of an amorphous product rendered impure by some Ser-Tyt. $[\alpha]_D^{20} = -31°$ (c = 1, in water).

 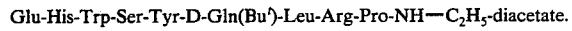
Glu-His-Trp-Ser-Tyr-D-Gln(Buᵗ)-Leu-Arg-Pro-NH—C₂H₅-diacetate.

250 mg of

 
Glu-His-Trp-NH—NH₂ are reacted in a manner analogous to that in Example 1f with 460 mg of H-Ser-Tyr-D-Gln(Buᵗ)-Leu-Arg-Pro-NH-C₂H₅ and converted into the acetate. The crude product is purified by gradient elution over carboxymethyl-cellulose (100 × 1.5 cm) with 0.002–0.01 n-ammonium acetate buffer as eluting agent. Yield: 213.5 mg of a thin layer chromatographically pure product (eluting agent 1). According to UV-spectrum: 63% peptide base.

Amino acid analysis (hydrolysis for 48 hours in 6n-HCl at 110° C):

Ser (0.8), Glu (1.95), Pro (1.0), Leu (1.0), Tyr (0.96), Bis (1.1), Arg (1.0). The Trp-content (1.0) was determined by UV-extinction.

EXAMPLE 5

Glu-His-Trp-Ser-Tyr-D-Gin(adamantyl)-Leu-Arg-Pro-NH—C₂H₅.

(a) Z-D-Gln(adamantyl)-OBzl

To a solution of 12.9 grams of Z-D-Glu-OBzl and 4.7 grams of 1-hydroxybenzotriazole in 100 ml of absolute tetrahydrofurane are added 6.53 grams of adamantylamine hydrochloride, 4.5 ml of N-ethylmorpholine and at 0° C. 7.65 grams of DCC. The mixture is stirred for 2 hours at 0° C. and allowed to stand overnight at room temperature. The next day the precipitate is filtered off with suction and the filtrate is concentrated. The residue is dissolved in ethyl acetate and the solution is washed in succession with a saturated solution of sodium bicarbonate, 2n-HCl, saturated sodium bicarbonate solution and water, dried with sodium sulphate and concentrated. The oily substance is purified over 150 grams of silica gel. Elution is carried out with 1 litre of methylene chloride and then with a mixture of methylene chloride/acetone (9:1) until the substance is eluted. Yield: 5.4 grams of an oil.

(b) 2-D-Gin(adamantyl)-OH. DCHA 5.4 Grams (10.7 mmol) of oily Z-D-Gln(adamantyl)-OBzl are dissolved in 50 ml of dioxane. 10 ml of water are added and titration is carried out with 1n-NaOH (indicator: thymolphthalein). Consumption: 10.5 ml of 1n-NaOH. Neutralisation is carried out with 2N-H₂SO₄ and the reaction mixture is concentrated. The residue is distributed between ethyl acetate and 2n-H₂SO₄. The ethyl acetate solution is dried with sodium sulphate and concentrated. The oily residue is dissolved in ether and dicyclohexylamine is added until the reaction is basic. The mixture is placed in a cool chamber overnight and on the next day the precipitate is filtered off with suction. It is washed with ether. Yield: 5.4 grams, melting point 170°.

(c) H-D-Gln(adamantyl)-Leu-Arg-Pro-NH-C₂H₅.2 HCl

5 Grams of Z-D-Gln(adamantayl)-OH·DCHA are distributed between ether and KHSO₄ solution. The ether phase is washed with water, dried with sodium sulphate and concentrated. The residue is dissolved in 30 ml of dimethylformamide together with 5.99 grams of H-Leu-Arg-Pro-NH-C₂H₅-ditosylate, 1.12 grams of 1-hydroxybenzotriazole and 2.15 ml of N-ethylmorpholine. 1.83 Grams of DCC are added at 0° C. and the mixture is stirred for one hour at 0° C. and overnight at room temperature. On the next day the precipitate is filtered off with suction, the filtrate is concentrated and the residue is triturated twice with saturated sodium bicarbonate solution. The residue is dissolved in methylene chloride, dried with sodium sulphate and concentrated. The residue is triturated with petroleum ether. Yield: 6 grams of an amorphous substance, which without further purification is catalytically hydrogenated in methanol in a manner analogous to that in Example 1d. The yield of chromatographically unitary substance after partitioning by partition chromatography in a manner analogous to that in Example 1e: 1.96 gram (eluting agent 2), [α]$_D^{20}$ = −55.1 (c=1, in methanol).

(d) H-Ser-Tyr-D-Gln(adamantyl)-Leu-Arg-Pro-NH-C₂H₅.2 HCl

To a solution of 1.95 grams of H-D-Gln(adamantyl)-Leu-Arg-Pro-NH-C₂H₅.2 HCl in 5 ml of dimethylformamide are added 0.68 ml of N-ethylmorpholine and 1.66 grams of Z-Ser-Tyr(Bzl)-OObt. The mixture is allowed to stand at room temperature overnight, concentrated and the residue is triturated twice with saturated sodium bicarbonate solution. The residue is dissolved in methylene chloride, and the solution is dried with sodium sulphate and concentrated. The residue is triturated with ether. Yield: 2.9 grams of an amorphous mass, which is catalytically hydrogenated in a methanol/dimethylformamide mixture (1:1) in a manner analogous to that in Example 1d. When the hydrogenation is complete, the catalyst is filtered off and the filtrate is concentrated. The residue is purified in a manner analogous to that in Example 1e by partition chromatography. Yield: 1.26 grams of a thin layer chromatographically unitary product (eluting agent 2) having the correct amino acid analysis.

(e)

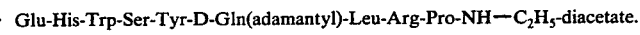
Glu-His-Trp-Ser-Tyr-D-Gln(adamantyl)-Leu-Arg-Pro-NH—C₂H₅-diacetate.

500 mg of

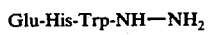
Glu-His-Trp-NH—NH₂ are reacted in a manner analogous to that in Example 1f with 997 mg of H-Ser-Tyr-D-Gln(adamantyl)-Leu-Arg-Pro-NH-C₂H₅.2 HCl and converted into the acetate. It is purified by gradient elution over carboxymethyl-cellulose (100 × 1.5 cm) with 0.002–0.01 n-ammonium acetate solution as eluting agent. Yield: 144 mg of a thin layer chromatographically unitary product (eluting agent 1). According to the UV-spectrum: 61% of peptide base.

Amino acid analysis (hydrolysis for 49 hours in 6n-HCl at 110° C.):

Ser (0.85), Glu (2.0), Pro (1.0), Leu (1.05), Tyr (0.85), His (0.95), Arg (1.0). The Trp-content (1.0) was determined by UV-extinction.

EXAMPLE 6

Glu-His-Trp-Ser-Tyr-D-Gln-Leu-Arg-Pro-NH—C₂H₅.

(a) H-Ser-Tyr-D-Gln-Leu-Arg-Pro-NH-C₂H₅.2 HCl 2.6 Grams of H-D-Gln(Mbh)-Leu-Arg-Pro-NH-C₂H₅.2 HCl are dissolved in a mixture of 1.3 ml of anisole and 13 ml of trifluoracetic acid. The mixture is allowed to stand for 2 hours at room temperature, concentrated at room temperature and the residue is triturated with ether. Yield: 2.0 grams of amorphous substance, which is dissolved in 10 ml of dimethylformamide with 1.6 grams of Z-Ser-Tyr(Bzl)-OH and 440 mg of 1-hydroxybenzotriazole. There are added 0.84 ml of N-ethylmorpholine and at 0° C. 717 mg of DCC, and the mixture is stirred for one hour at 0° C. and allowed to stand overnight at room temperature. On the next day the precipitate is filtered off with suction and the filtrate is concentrated. The residue is triturated twice with saturated sodium bicarbonate solution. Distillation with absolute alcohol is carried out and the residue is triturated with ether. Yield: 2.9 grams of an amorphous substance, which is catalytically hydrogenated in a methanol-dimethylformamide mixture (1:1) in a manner analogous to that in Example 1d. When the hydrogenation is complete, the catalyst is filtered off and the filtrate is concentrated. The residue is purified by partition chromatography in a manner analogous to that in Example 1e. Yield of thin layer chromatographically unitary substance (eluting agent 2): 870 mg. $[\alpha]_D^{20} = -39.5°$ (c = 1, in methanol).

(b)

Glu-His-Trp-Ser-Tyr-D-Gln-Leu-Arg-Pro-NH—C$_2$H$_5$-diacetate.

250 mg of

Glu-His-Trp-NH—NH$_2$ are reacted in a manner analogous to that in Example 1f with 430.9 mg of H-Ser-Tyr-D-Gln-Leu-Arg-Pro-NH-C$_2$H$_5$.2 HCl and the reaction product is converted into the acetate. The crude substance is purified by gradient elution over carboxymethyl-cellulose (100 × 1.5 cm) with 0.002-0.01 n-ammonium acetate buffer as eluting agent. Yield: 256 mg. content of peptide base according to UV-spectrum: 82%.

Amino acid analysis (hydrolysis for 65 hours in 6n-HCl at 110° C):

Ser (0.77), Glu (2.0), Pro (0.95), Leu (1.0), Tyr (0.95), His (1.2), Arg (1.0). the Trp-content (1.0) was determined by UV-extinction.

mamide mixture (1:1), and catalytically hydrogenated in a manner analogous to that in Example 1d. When the hydrogenation is complete, the catalyst is filtered off with suction and the filtrate is concentrated. The residue is triturated with ether. Yield: 3.4 grams melting at 110°-113°, $[\alpha]_D^{20} = -41.8°$ (c = 1, in methanol).

(c) Z-Ser-Tyr(Bzl)-D-Gln(Mbh)-Leu-Arg-Pro-cyclopropylamide

To a solution of 3.1 grams of H-D-Gin(Mbh)-Leu-Arg-Pro-cyclopropylamide.2 HCl, 1.8 grams of Z-Ser-Tyr(Bzl)-OH and 493 mg of 1-hydroxybenzotriazole are added 0.95 ml of N-ethylmorpholine and at 0° C. 803 mg of DCC, and the mixture is stirred for one hour at 0° C. and allowed to stand overnight at room temperature. The precipitate is filtered off with suction and the filtrate is distributed between 150 ml of n-butanol and 130 ml of sodium chloride solution. The n-butanol phase is extracted by agitation twice with 75 ml of saturated sodium bicarbonate solution each time and concentrated. The residue is triturated with ether and filtered off with suction. Yield: 4.1 grams, melting at 133°-135°, $[\alpha]_D^{20} = -21.1°$ (c = 1, dimethylacetamide).

(d) Z-Ser-Tyr(Bzyl)-D-Gln-Leu-Arg-Pro-cyclopropylamide 3.6 Grams of Z-Ser-Tyr(Bzl)-D-Gln(Mbn)-Leu-Arg-Pro-cyclopropylamide are dissolved with 2 ml of anisole in 20 ml of trifluoracetic acid. The mixture is allowed to stand for 3 hours at room temperature, concentrated and the residue is triturated with ether. Yield: 2.7 grams, melting at 145°-148°.

(e) H-Ser-Tyr-D-Gln-Leu-Arg-Pro-cyclopropylamide.2 HCl 2.7 Grams of Z-Zer-Tyr(Bzl)-D-Gln-Leu-Arg-Pro-cyclopropylamide are catalytically hydrogenated in methanol in a manner analogous to that in Example 1d. When the hydrogenation is complete, the catalyst is filtered off with suction and the filtrate is concentrated. The residue is triturated with ether and filtered off with suction.

Yield: 1.95 grams, melting at 137°-140°, $[\alpha]_D^{20} = -36.1°$ (c = 1, in dimethylacetamide).

(f)

Glu-His-Trp-Ser-Tyr-D-Gln-Leu-Arg-Pro-cyclopropylamide-diacetate.

EXAMPLE 7

Glu-His-Trp-Ser-Tyr-D-Gln-Leu-Arg-Pro-cyclopropylamide.

(a) Z-D-Gln(Mbh)-Leu-Arg-Pro-cyclopropylamide

To a solution of 2.5 grams of H-Leu-Arg-Pro-cyclopropylamide.2 HCl and 675 mg of 1-hydroxybenzotriazole in 10 ml of dimethylformamide are added 1.3 ml of N-ethylmorpholine and 3.43 grams of Z-D-Gln(Mbh)-OTcp. After one hour the solution is distributed between 100 ml of n-butanol and 100 ml of sodium chloride solution. The n-butanol phase is extracted by agitation twice with 100 ml of saturated sodium bicarbonate solution and once with 50 ml of water and then concentrated. The residue is triturated with ether.

Yield: 4.7 grams, melting at 160°-165°, $[\alpha]_D^{20} = -13.9°$ (c = 1) in diemthylacetamide).

(b) H-D-Gln(Mbh)-Leu-Arg-Pro-cyclopropylamide 4.3 Grams of Z-D-Gln(Mbh)-Lue-Arg-Pro-cyclopropylamide are dissolved in a methanol-dimethylfor- 250 mg of

Glu-His-Trp-NH—NH$_2$ are reacted in a manner analogous to that in Example 1f with 437.5 mg of H-Ser-D-Gln-Leu-Arg-Pro-cyclopropylamide.2 HCl and the resulting product is converted into the acetate. The crude product is purified by partition chromatography in a manner analogous to that in Example 1e. Yield: 212 mg of a thin layer chromatographically unitary product (eluting agent 1). Content of peptide base according to UV-spectrum: 86%, $[\alpha]_D^{20} = -42.4°$ (c = 1, in water).

EXAMPLE 8

⌐Glu-His-Trp-Ser-Tyr-D-Gln-Cys(Bu$^t$)-Arg-Pro-cyclopropylamine.

(a) H-Cys-(Bu$^t$)-Arg-Pro-cyclopropylamide.2 HCl

To a solution of 5.51 grams of H-Arg-Pro-cyclopropylamide.2HCl and 2.5 grams of 1-hydroxybenzotriazole in 50 ml of dimethylformamide are added at room temperature 4.8 ml of N-ethylmorpholine and 8.45 grams of Boc-Cys(Bu$^t$)-OTcp. The mixture is allowed to stand overnight at room temperature, and the solution is distributed between 150 ml of n-butanol and 150 ml of saturated sodium chloride solution. The n-butanol phase is extracted by agitation twice with saturated sodium bicarbonate solution and concentrated. The residue (12.4 grams) is dissolved in 55 ml of 6n HCL/dioxane solution at room temperature. The mixture is allowed to stand for 2 hours at room temperature, concentrated and the residue is triturated with ether. Yield: 7.5 grams, $[\alpha]_D^{20} = -33.9°$ (c = 1, in methanol).

(b) H-D-Gln(Mbh)-Cys(Bu$^t$)-Arg-Pro-cyclopropylamide.2 HCl

To a solution of 2.7 grams of H-Cys(Bu$^t$)-Arg-Pro-cyclopropylamide.2 HCl and 6.75 mg of 1-hydroxybenzotriazole in 10 ml of dimethylformamide are added at room temperature 1.3 ml of N-ethylmorpholine and 3.42 grams of Z-D-Gln(Mbh)-OTcp. After a reaction period of 2 hours, the solution is distributed between 75 ml of n-butanol and 75 ml of saturated sodium chloride solution. The n-butanol phase is extracted by agitation twice with a saturated sodium bicarbonate solution and concentrated. The residue is triturated with ether and filtered off with suction. The resulting 4.8 grams of substance are catalytically hydrogenated in a manner analogous to that in Example 1d in a methanol-dimethylformamide mixture (1:1). The catalyst is filtered off with suction and the filtrate is concentrated. The residue is purified by partition chromatography in a manner analogous to that in Example 1e. Yield: 1.2 grams of chromatographically unitary substance (eluting agent 2), $[\alpha]_D^{20} = -52.4°$ (c = 1, in methanol).

(c) Z-Ser-Tyr(Bzl)-D-Gln(Mbh)-Cys(Bu$^t$)-Arg-Pro-cyclopropylamide to a solution of 704 mg of Z-Ser-Tyr(Bzl)-OH and 233 mg of 3-hydroxy-4-oxo-3,4-dihydro-1,2,3-benzotriazine in 10 ml of tetrahydrofurane are added at 0° C. 3.5 mg of DCC, and the mixture is stirred for one hour at 0° C and one hour at room temperature. There are then added 1.16 grams of H-D-Gln(Mbh)-Cys(Bu$^t$)-Arg-Pro-cyclopropylamide.2 HCl in 10 ml of dimethylformamide and 0.39 ml of N-ethylmorpholine. After one hour at room temperature, the precipitate is filtered off with suction and washed with dimethylformamide. The tetrahydrofurane is distilled off in vacuo, and the dimethylformamide solution (30 ml) that remains is distributed between 100 ml of n-butanol and 100 ml of saturated sodium bicarbonate solution. The n-butanol phase is extracted by agitation twice with saturated sodium bicarbonate solution. The solution, from which the peptide has already precipitated, is concentrated and the residue is extracted at the boil with ethyl acetate and filtered off with suction. Yield: 1.6 grams, melting at 176°-180°, $[\alpha]_D^{20} = -25.5°$ (c = 1, in dimethylacetamide.

(d) H-Ser-Tyr-D-Gln-Cys(Bu$^t$)-Arg-Pro-cyclopropylamide.2 HCl 1.6 Grams of Z-Ser-Tyr(Bzl)-D-Gln(Mbh)-Cys(Bu$^t$)-Arg-Procyclopropylamide and 1 ml of anisole are dissolved in 10 ml of trifluoroacetic acid. The mixture is allowed to stand for 3 hours at room temperature, concentrated in vacuo and the residue is triturated with ether. The resulting 1.3 grams are catalytically hydrogenated in a manner analogous to that in Example 1d in a methanol-dimethylformamide mixture. The catalyst is filtered off with suction, the filtrate is concentrated and the residue is triturated with ether. Yield: 1.2 grams, $[\alpha]_D^{20} = -29.1°$ (c = 1, in dimethylacetamide).

(e)

⌐Glu-His-Trp-Ser-Tyr-D-Gln-Cys(Bu$^t$)-Arg-Pro-cyclopropyl-amide diacetate.

500 mg of

⌐Glu-His-Trp-NH—NH$_2$ are reacted in a manner analogous to that in Example 1f with 921 mg of H-Ser-Tyr-D-Gln-Cys(Bu$^t$)-Arg-Pro-cyclopropylamide.2 HCl and converted into the acetate. The crude product is purified by partition chromatography in a manner analogous to that in Example 1e and by gradient elution over carboxymethyl-cellulose (100 × 1.5 cm) with 0.002 –0.01 m-ammonium acetate solution as eluting agent. Yield: 224 mg, $[\alpha]_D^{20} = -29.6°$ (c = 1, in water). Content of peptide base according to UV-spectrum: 85%.

Amino acid analysis (Hydrolysis for 65 hours in 6n-HCl at 110° C.):

Ser (0.65), Glu (2.00), Cys (0.92), Tyr (1.00), His(1.01) Arg (1.02). The Trp-content (1.0) was determined by UV-extinction.

EXAMPLE 9

⌐Glu-His-Trp-Ser-Tyr-D-Gln-Cys(Bu$^t$)-Arg-Pro-NH—C$_2$H$_5$.

(a) Z-D-Gln(Mbh)-Cys(Bu$^t$)-Arg-Pro-NH-C$_2$H$_5$

To a solution of 2.65 grams of H-Cys(Bu$^t$)-Arg-ProNH-C$_2$H$_5$.2 HCl and 675 mg of HOBt in 10 ml of dimethylformamide are added 1.3 ml of N-ethylmorpholine and 3.42 grams of Z-D-Gln(Mbh)-OTcp. After a reaction period of 2 hours, working up is carried out in a manner analogous to that in Example 8b. Yield: 3.9 grams, $[\alpha]_D^{20} = -26.9°$ (c = 1, in methanol).

(b) H-D-Gln(Mbh)-Cys(Bu$^t$)-Arg-Pro-NH-C$_2$H$_5$.2 HCl 3.9 Grams of Z-D-Gln(Mbh)-Cys(Bu$^t$)-Arg-Pro-NH-C$_2$H$_5$ are catalytically hydrogenated in a manner analogous to that in Example 1d in a methanol-dimethylformamide mixture. The catalyst is filtered off with suction and the filtrate is concentrated. Yield: 2.8 grams. The substance is purified by partition chromatography in a manner analogous to that in Example 1e. Yield: 1.27 grams, $[\alpha]_D^{20} = -58.8°$ (c = 1, in methanol).

(c) Z-Ser-Tyr(Bzl)-D-Gln(Mbh)-Cys(Bu$^t$)-Arg-Pro-NH-C$_2$H$_5$.

704 mg of Z-Ser-Tyr(Bzl)-OH are reacted in a manner analogous to that in Example 8c with 1.15 grams of H-D-Gln(Mbh)Cys(Bu$^t$)-Arg-Pro-NH-C$_2$H$_5$. Yield: 1.75 grams, melting at 175°–181°, $[\alpha]_D^{20} = -20.9°$ (c = 1, in dimethylacetamide).

(d) H-Ser-Tyr-D-Gln-Cys(Bu$^t$)-Arg-Pro-NH-C$_2$H$_5$.2 HCl 1.75 Grams of Z-Ser-Tyr(Bzl)-D-Gln(Mbh)-Cys(-Bu$^t$)-Arg-Pro-NH-C$_2$H$_5$ are catalytically hydrogenated in a manner analogous to that in Example 1d in a methanol-dimethylformamide mixture (1:1). The catalyst is filtered off with suction and the residue is triturated with ether. The resulting 1.64 grams are dissolved with 1 ml of anisole in 10 ml of trifluoracetic acid. The mixture is allowed to stand for 3 hours at room temperature, concentrated and the residue is triturated with ether. Yield: 1.5 grams, $[\alpha]_D^{21} = -21.3°$ (c = 1, in dimethylacetamide).

(e) H-Trp-Ser-Tyr-D-Gln-Cys(Bu$^t$)-Arg-Pro-NH-C$_2$H$_5$.2 HCl

To a solution of 1.5 grams of H-Ser-Tyr-D-Gln-Cys(-Bu$^t$)-Arg-Pro-NH-C$_2$H$_5$.2 HCl and 238 mg of HOBt in 5 ml of dimethylformamide are added at room temperature 0.46 ml of N-ethylmorpholine and 912 mg of Z-Trp-OTcp. After a reaction period of 2 hours at room temperature, the reaction solution is distributed between 60 ml of n-butanol and 60 ml of saturated sodium bicarbonate solution. The n-butanol phase is extracted by agitation twice with sodium bicarbonate solution, concentrated in vacuo and triturated with ether. The resulting 1.35 grams of substance are catalytically hydrogenated in a manner analogous to that in Example 1d in a methanol-dimethylformide mixture. The catalyst is filtered off with suction and the filtrate is concentrated. The residue is purified by partition chromatography in a manner analogous to that in Example 1e. Yield: 340 mg of thin layer chromatographically unitary product (eluting agent 2).

(f)

Glu-His-Trp-Ser-Tyr-D-Gln-Cys(Bu$^t$)-Arg-Pro-NH—C$_2$H$_5$-diacetate.

To a solution of 75.5 grams of

Glu-His-OH, 34 mg HOBt and 274 mg of H-Trp-Ser-Tyr-D-Gln-Cys(Bu$^t$)-Arg-Pro-NH-C$_2$H$_5$.2 HCl and 0.065 ml of N-ethylmorpholine in 1.5 ml of dimethylacetamide are added at 0° C. 55 mg of DCC, and the mixture is stirred for one hour at 0° C. and overnight at room temperature. On the next day a further 7.5 mg of

Glu-His-OH and 27.5 mg of DCC are added. The mixture is stirred for one day at room temperature, and the precipitate is filtered off with suction and washed with dimethylacetamide. The dimethylacetamide solution is distributed between 30 ml of n-butanol and 30 ml of saturated sodium bicarbonate solution. The n-butanol phase is extracted twice by agitation portions with 30 ml of sodium bicarbonate solution and once with water, and concentrated. The residue is converted into the acetate in the manner to that in Example 1f. The crude product is purified by partition chromatography in a manner analogous to that in Example 1e. Yield: 58 mg, Peptide content according to the UV-spectrum: 71%.

Amino acid analysis (hydrolysis for 65 hours in 6n-HCl at 110° C.):

Ser (0.70), Glu (2.00), Cys (0.91), Tyr (0.96), His (1.00), Arg (1.01). The Trp-content was determined by UV-extinction (1.0).

EXAMPLE 10

Glu-His-Trp-Ser-Tyr-D-Gln-Leu-Arg-Pro-Gly-NH$_2$.

(a) Z-D-Gln(Mbh)-Leu-Arg-Pro-Gly-NH$_2$

To a solution of 3.75 grams of H-Leu-Arg-Pro-Gly-NH$_2$-ditosylate and 675 mg of HOBt in 10 ml of dimethylformamide are added 3.42 grams of Z-D-Gln(Mbh)-OTcp. After a reaction period of two hours, the solution is concentrated, the residue is triturated with a saturated sodium bicarbonate solution and filtered off with suction. Yield: 5.5 grams, melting at 175°–178°, $[\alpha]_D^{20} = -13.1°$ (c = 1, in dimethylacetamide).

(b) H-D-Gln(MbH-Leu-Arg-Pro-Gly-NH$_2$.2 HCl 5.5 Grams of Z-D-Gln(Mhb)-Leu-Arg-Pro-Gly-NH$_2$ are catalytically hydrogenated in a manner analogous to that in Example 1d in a methanol-dimethylformamide mixture. The catalyst is filtered off with suction, the filtrate is concentrated and the residue is triturated with ether. Yield: 4.0 grams, $[\alpha]_D^{20} = -28.4°$ (c = 1, in dimethylacetamide).

(c) Z-Ser-Tyr(Bzl)-D-Gln(Mbh)-Leu-Arg-Pro-Gly-NH$_2$ 2.16 Grams of Z-Ser-Tyr(Bzl)-OH are reacted in a manner analogous to that in Example 8c with 3.47 grams of H-D-Gln-(Mbh)-Leu-Arg-Pro-Gly-NH$_2$.2 HCl. Yield: 5.2 grams, $[\alpha]_D^{20} = -14.5°$ (c = 1, in dimethylacetamide). (d) H-Ser-Tyr-D-Gln-Leu-Arg-Pro-Gly-NH$_2$.2 HCl 5.2 Grams of Z-Ser-Tyr(Bzl)-D-Gln(Mbh)-Leu-Arg-Pro-Gly-NH$_2$ are dissolved with 3 ml of anisole in 30 ml of trifluoracetic acid. The mixture is allowed to stand for 3 hours at room temperature, concentrated in vacuo, and the residue is triturated with ether. The resulting 6.4 grams are catalytically hydrogenated in a manner analogous to that in Example 1d in methanol. The catalyst is filtered off with suction and the filtrate is concentrated. The residue is triturated with ether, and then purified by partition chromatography in a manner analogous to that in Example 1e. Yield: 1.3 grams, $[\alpha]_D^{20} = -43.6°$ (c = 1, in methanol).

(e)  Glu-His-Trp-Ser-Tyr-D-Gln-Leu-Arg-Pro-Gly-NH$_2$.

500 mg of

 Glu-His-Trp-NH—NH$_2$ are reacted in a manner analogous to that in Example 1f with 892 mg of H-Ser-Tyr-D-Gln-Leu-Arg-Pro-Gly-NH$_2$.2 HCl, and converted into the acetate. The crude product is purified by partition chromatography in a manner analogous to that in Example 1e and by gradient elution over carboxymethyl-cellulose (100 × 1.5 cm) with 0.002–0.01 m-ammonium acetate solution as eluting agent. Yield: 240 mg, $[\alpha]_D^{20} = -41.4°$ (c = 1, in water). Content of peptide base accoding to UV-spectrum: 92%. Amino acid analysis (hydrolysis for 65 hours in 6n-HCl at 110° C.).

EXAMPLE 11

 Glu-His-Trp-Ser-Tyr-D-Glu(Gly-testosterone ester)-Leu-Arg-Pro-NH—C$_2$H$_5$.

(a) Glycine-testosterone ester trifluoracetate

To a suspension of 0.85 gram (5.25 mmol) of carbonyl-diimidazole in 5 ml of absolute tetrahydrofurane is added at room temperature 0.79 grams (5 mmol) of Boc-glycine. After a reactionperiod of 15 minutes, 1.44 grams (5 mmol) of testosterone are added. After 1.5 hours, 1.5 ml of a solution of 11.5 mg of sodium and 115 mg of imidazole in 15 ml of tetrahydrofurane are added. Reaction is carried out for a further hour at room temperature, the mixture is concentrated and the residue is taken up in ethyl acetate. The ethyl acetate solution is extracted by agitation with KHSO$_4$ solution, a saturated solution of sodium bicarbonate and water, dried with sodium sulphate and concentrated. The residue is dissolved in 5 ml of trifluoracetic acid. The solution is allowed to stand for 30 minutes at room temperature and concentrated. The residue is triturated with ether. Yield: 1.3 grams, melting at 159°–164°.

(b)

 Glu-His-Trp-Ser-Tyr$^D$-Glu(Gly-testosterone ester)-Leu-Arg-Pro-NH—C$_2$H$_5$ . 2 HCl.

90 mg of Glu-His-Trp-Ser-Tyr-D-Glu-Leu-Arg-Pro-NH-C$_2$H$_5$-diacetate, 70.2 mg of glycine-testosterone ester trifluoracetate, 20 mg of 1-hydroxybenzotriazole and 0.04 ml of N-ethylmorpholine are disslved in 1 ml of dimethylformamide. 34 mg of DCC are added and the whole is allowed to stand overnight at room temperature. On the next day the precipitate is filtered off with suction, the filtrate is concentrated and the residue is triturated with ether. The product is dissolved in a small amount of methanol. 0.67 ml of 0.23n-methanolic hydrochloric acid is added and the solution is concentrated. The crude substance is purified chromatographically over a column of silica gel. As eluting agent the following mixture was used: Chloroform/methanol/acetic acid/water water as 10:4:0.9:0.9. 32 mg of chromatographically pure product (eluting agent 1) are obtained. Content of peptide base according to amino acid analysis: 70%.

Amino acid analysis (hydrolysis for 68 hours in 6n-HCl at 110° C.):

Ser (0.6), Glu (1.93), Gly (1.1), Leu (1.0), Tyr (1.0), His (1.1), Arg (0.97).

EXAMPLE 12

 Glu-His-Trp-Ser-Tyr-D-Gln(C$_2$H$_5$)-Leu-Arg-Pro-NH—C$_2$H$_5$.

To a solution of 122 mg of

 Glu-His-Trp-Ser-Tyr-D-Glu-Leu-Arg-Pro-NH—C$_2$H$_5$-diacetate, 8.2 mg of ethylamine hydrochloride and 27.5 mg of 1-hydroxybenzotriazole in 1 ml of dimethylacetamide are added 0.065 ml of N-ethylmorpholine and at 0° C. 66 mg of DCC, and the mixture is stirred for 1 hour at 0° C. and overnight at room temperature. On the next day the precipitate is filtered off with suction, the filtrate is concentrated and the residue is triturated with ether. The crude product is purified in a manner analogous to that in Example 1e by partition chromatography. Yield: 40.2 mg, Content of peptide base accordint to UV-spectrum: 85%.

Amino acid analysis (hydrolysis for 65 hours in 6n-HCl at 110° C.):

Ser (0.73), Glu (1.90), Pro (1.00), Leu (0.90), Tyr (0.80), His (1.00), Arg (1.02). The Trp-content (1.0) was determined by UV-extinction.

EXAMPLE 13

Preparation for oral use.

10 Grams of

 Glu-His-Trp-Ser-Tyr-D-Gln-Leu-Arg-Pro-NH—C$_2$H$_5$-diacetate are triturated with 542 grams of lactose. The triturate is mixed with 300 grams of potato starch, moistened with an alcoholic solution of 8 grams of gelatine and granulated. After drying, the mixture is admixed with 60 grams of potato starch, 10 grams of magnesium stearate, 20 grams of highly dispersed silicone oxide and 60 grams of talcum, and the mixture is pressed to form 10,000 tablets each weighing 150 mg. Each tablet contains 1 mg of active substance.

EXAMPLE 14

Preparation for intranasal use 4.0 Grams of

are dissolved in 100 ml of distilled water. At the same time 31.2 grams of $NaHPO_4.2H_2O$, 66.29 grams of $Na_2HPO_4$, 25 grams of NaCl and 100 grams of benzyl alcohol are dissolved in 8 liters of distilled water, and 500 grams of polyvinyl alcohol having a K-value of about 90 are added. The two solutions are combined and filtered. The individual dose of 20 μ grams is contained in 0.05 ml.

EXAMPLE 15

Preparation for intranasal use

100 Grams of anhydrous lanolin and 440 grams of petroleum jelly are melted together. To the cooled melt is added a suspension of 800 mg of microfine

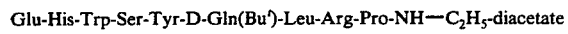

in 359.2 grams of liquid paraffin. Finally, 10 grams of benzyl alcohol are added and the salve is homogenised. The individual dose of 40 μ grams is contained in 0.05 grams of salve.

EXAMPLE 16

Preparation for injections 2 mg of

are dissolved in 500 ml of bi-distilled water and 100 ml of phosphate buffer pH 4.5 are added. Then 1 gram of mannite and the quantity of NaCl calculated for isotonicity are added and made up with water to 1 liter. After sterile filtration, the preparation is charged into ampoules at 1 and 2 ml and lyophilised.

EXAMPLE 17

Preparation for injections

The procedure is according to Example 16, but before making up the mixture with water, 2.5 grams of 4-hydroxybenzoic acid methyl ester are added. After sterile filtration, the preparation is charged into ampoules at 1 or 2 ml.

We claim:

1.

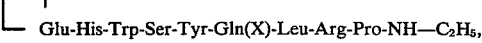

wherein X is cyclohexyl, adamantyl, or 4,4'-dimethoxybenzhydryl.

2.

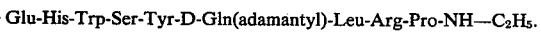

3.

4.

5. A pharmaceutical preparation having LH— and FSH— releasing activity, said preparation comprising an effective amount of a compound as in claim 3 in combination with a carrier.

6. The method of stimulating the release of the luteinizing hormone and follicle stimulating hormone in a patient, which method comprises administering to said patient an effective amount of a compound as defined in claim 3.

* * * * *